United States Patent [19]

Grossman

[11] Patent Number: 4,713,547

[45] Date of Patent: Dec. 15, 1987

[54] METHOD AND APPARATUS FOR MONITORING THE FLOW OF MERCURY IN A SYSTEM

[75] Inventor: Mark W. Grossman, Belmont, Mass.

[73] Assignee: GTE Products Corporation, Danvers, Mass.

[21] Appl. No.: 816,035

[22] Filed: Jan. 3, 1986

[51] Int. Cl.$^4$ ............................................. G01N 21/59
[52] U.S. Cl. ..................................... 250/373; 250/372
[58] Field of Search ................ 250/373, 372; 356/246, 356/436

[56] References Cited

U.S. PATENT DOCUMENTS

| | | | |
|---|---|---|---|
| 3,521,964 | 7/1970 | Wilks | 356/246 |
| 3,778,162 | 12/1973 | Gant et al. | 250/373 |
| 4,023,909 | 5/1977 | Ross | 356/246 |

FOREIGN PATENT DOCUMENTS 2133797  1/1973  Fed. Rep. of Germany ...... 356/436

OTHER PUBLICATIONS

Holden et al., "Variable Thick . . . IR Cell", Journal Optic, Soc. of Amer., 40, No. 11, 757, (1950).
Yanabe, et al., "VUV Atom. Abs. Spect. of Hg", Anal. Chem. 52, pp. 453-457, Mar. 1980.
Webster et al., "Photochem. Iot. Sep. of Hg . . . ", J. Phys. Chem., 85, 1302, (1981).
Osborn et al., "Determ. of Hg-202 . . . by Hg Reson. Rad. Absorb.", J. Opt. Soc. of Am., 45, 552, (1955).
Zemansky, "Absorption & Coll. Broad of Hg-Line", Physical Rev., 36, 249, (1930).

Primary Examiner—Janice A. Howell
Assistant Examiner—Richard Hanig
Attorney, Agent, or Firm—Martha Ann Finnegan

[57] ABSTRACT

An apparatus and method for monitoring the flow of mercury in a system. The equipment enables the entrainment of the mercury in a carrier gas e.g., an inert gas, which passes as mercury vapor between a pair of optically transparent windows. The attenuation of the emission is indicative of the quantity of mercury (and its isotopes) in the system. A 253.7 nm light is shone through one of the windows and the unabsorbed light is detected through the other window. The absorption of the 253.7 nm light is thereby measured whereby the quantity of mercury passing between the windows can be determined. The apparatus includes an in-line sensor for measuring the quantity of mercury. It includes a conduit together with a pair of apertures disposed in a face to face relationship and arranged on opposite sides of the conduit. A pair of optically transparent windows are disposed upon a pair of viewing tubes. A portion of each of the tubes is disposed inside of the conduit and within each of the apertures. The two windows are disposed in a face to face relationship on the ends of the viewing tubes and the entire assembly is hermetically sealed from the atmosphere whereby when 253.7 nm ultraviolet light is shone through one of the windows and detected through the other, the quantity of mercury which is passing by can be continuously monitored due to absorption which is indicated by attenuation of the amplitude of the observed emission.

21 Claims, 4 Drawing Figures

DISPLACEMENT FROM "O" (GHz)

$Hg(6^1S_0 \leftarrow 6^3P_1)$

METHOD AND APPARATUS FOR MONITORING THE FLOW OF MERCURY IN A SYSTEM

The government has rights to this invention, pursuant to subcontract number 4524210 under Prime Contract DE-AC03-76SF00098 awarded by the U.S. Department of Energy.

FIELD OF THE INVENTION

This invention relates to in-line sensors and particularly to a sensor that can continuously monitor the quantity of mercury and mercury isotapes passing through a system.

BACKGROUND OF THE INVENTION

In-line sensors are well known to the art and measurements have previously been made to determine the quantity of mercury in a system. Heretofore, however, the principle approach to measuring the quantity of mercury in a system was to weigh the feedstock before a process step took place and then weigh it again afterwards. Such procedures can produce large discrepancies and errors, frequently as high as + or −36%.

SUMMARY OF THE INVENTION

In accordance with one aspect of the present invention, there is provided a sensor apparatus for measuring the quantity of mercury passing through a system, adapted for use with a narrow wavelength ultraviolet light beam source and an ultraviolet light detector said sensor comprising: means for forming a conduit for conveying mercury; a pair of apertures disposed face to face and arranged on opposite sides of said conduit; a pair of hollow support means, a portion of each being disposed inside of said conduit means and within one of said apertures; a pair of optically transparent windows, one of said windows being disposed upon each of the internal ends of said hollow support means; means for adjusting the relative distance between the faces of said optically transparent windows; means for forming a vacuum seal; means for passing a narrow wavelength ultraviolet light beam through one of said windows, through the space between said windows, and the through the other of said windows; and means for passing the ultraviolet light passing through the other of said windows to an ultraviolet light detector whereby absorption of the ultraviolet light is continuously measured thereby giving an indication of the quantity of mercury passing between said windows.

In accordance with another aspect of the present invention there is provided a sensor system for measuring the quantity of mercury passing through a system, said sensor comprising: means for forming a conduit for conveying mercury; a pair of apertures disposed face to face and arranged on opposite sides of said conduit; a pair of hollow support means, a portion of each being disposed inside of said conduit means and within one of said apertures; and a pair of optically transparent windows, one of said windows being disposed upon each of the internal ends of said hollow support means; means for adjusting the relative distance between the faces of said optically transparent windows; and means for forming a vacuum seal; and means for generating a narrow band width of ultraviolet light; and means for passing said narrow wavelength ultraviolet light beam through one of said windows, through the space between said windows and then through the other of said windows; and means for detecting the ultraviolet light passing through the other window whereby absorption of the ultraviolet light is continuously measured thereby giving an indication of the quantity of mercury passing between said windows.

In accordance with still a further aspect of the present invention there is provided a method of continuously monitoring the quantity of mercury flowing through a system, said method comprising: passing mercury enrained in a carrier gas between a pair of windows optically transparent to ultraviolet light; and transmitting ultraviolet light through one of said windows and receiving ultraviolet light through the other of said windwos, said light passing through said entrained mercury whereby some of said light is absorbed by the mercury passing there between; and measuring the quantity of ultraviolet light absorbed by the mercury passing between said windows whereby to continuously indicate the quantity of mercury flowing through the system.

Figure 1:
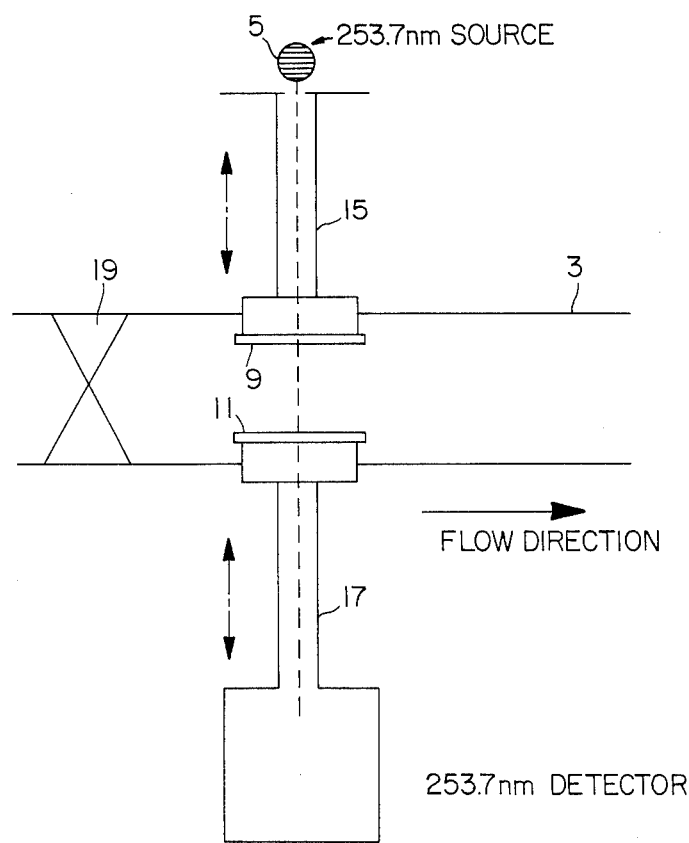
FIG. 1 is a schematic view of an in-line mercury flow monitor and sensor according to the present invention.

For a better understanding of the present invention, together with other and further objects, advantages, and capabilities thereof, reference is made to the following disclosure and appended claims in connection with the above-described drawings.

DESCRIPTION OF THE PREFERRED EMBODIMENTS

As has been disclosed to the art in the patent to Work et al U.S. Pat. No. 4,379,252, if the 196 isotope of mercury is increased in concentration relative to natural mercury, that is from about 0.15% to about 3%, ultraviolet light generation at 253.7 nm is increased in a low pressure discharge. When such enriched mercury is used in a fluorescent lamp with conventional phosphors, high lumens per watt are produced. In the separation of mercury isotopes for use in such lamps, the rate at which the mercury feedstock passes through the reaction zone is an important parameter and it is highly desirable to monitor it continuously. For such monitoring, I have found that the amount of absorption of the 253.7 nm light is related to the quantity of mercury passing in suspension between the two windows in the mercury sensor. If the mercury is entrained in a carrier gas and pumped between them, absorption of the mercury passing between the windows can be continuously measured thereby giving a measurement of the amount of mercury passing through the system. Moreover, since the concentrations of isotopic mercury can be closely estimated in any given sample of "natural" mercury, a measurement of the total mercury passing through the monitoring device of the present invention can be indicative of the quantity of the mercury isotope that is present. In the alternative, when using light sources formed of the various isotopes, a precise measurement of the concentration of these isotopes can be made in the sensor.

The principle of operation of the flow monitor relies on the assumption of "perfect entrainment" and "plug" flow of mercury vapor and carrier gas. As described below, the location of the monitor downstream of the throttle valve is imperative in order to correlate changes in the transmitted radiation and changes in mercury flow rate.

The following terms are defined:
$V_{Hg}$ = velocity of mercury vapor
$V_{Gas}$ = velocity of carrier gas
$Q_{Hg}$ = mercury flow rate
$Q_{Gas}$ = carrier gas flow rate
$N_{Hg}$ = mercury vapor density
$N_{Gas}$ = carrier gas density
$P_{Hg}$ = mercury vapor pressure
$P_{Gas}$ = gas pressure
$A$ = cross-sectional area of reactor through which gas and vapor flows For perfect entrainment $$V_{Hg} = V_{Gas} \quad (1)$$

For plug flow $$Q_{Hg} = N_{Hg} V_{Hg} A \quad (2a)$$

and $$Q_{Gas} = N_{Gas} V_{Gas} A \quad (2b)$$

Thus a simple relationship is obtained
$$Q_{Hg} = Q_{Gas} \cdot N_{Hg}/N_{Gas} \quad (3)$$

For sufficiently small values of $N_{Hg}$ (See M.W. Zemansky, Physical Review 36, 249 (1930), which is hereby incorporated by reference, and the calibration curve) the absorption of radiation is proportional to $N_{Hg}$ and thus according to (3) $Q_{Hg}$. Equation (3) describes the basic principle of operation of the flow monitor. As $N_{Hg}$ increases, a non-linearity can develop requiring a calibration curve between radiation absorption and $N_{Hg}$. Furthermore, if the flow monitor is upsteam of the throttle valve, changing the throttle valve position changes $N_{Gas}$ and according to (3) (verified by experimental data), $Q_{Hg}$ changes. However, the flow monitor only senses changes in $N_{Hg}$ and this may or may not occur upstream of the throttle valve. On the other hand, placing the flow monitor downstream of the throttle valve ensures that as the throttle valve position changes $N_{Gas}$ is unchanged at the downstream location of the flow monitor. Thus, in steady state operation, changes in $Q_{Hg}$ are independent of upstream changes in $N_{Gas}$ provided the flow monitor is positioned downstream of the throttle valve. And in this case, monitoring the changes in absorption of radiation can be correlated to changes only in $Q_{Hg}$.

Referring now to FIG. 1, a 253.7 nm source 1 is shown on one side of a conduit 3. The source 1 can be an RF/coupled quartz jacketed lamp 5. Disposed on the side of the conduit 3 is a 253.7 nm detector 7 which can be a 0.2 meter double pass Y monochrometer utilizing a standard UV sensitive photomultiplier tube and a picoammeter. An X/Y chart recorder receives an analog signal from the monochrometer and records it whereby a display can be made of the quantity of mercury passing between two windows 9 and 11 that are optically transparent to ultraviolet light. Preferably, the windows 9 and 11 are thin quartz glass, generally less than about 0.1 cm. thick. They are arranged so as to be separated from each other by a distance between about 0.0 to 1.5 cm and can be adjusted by moving tubes 15 and 17 relative to each other so as to insert or withdraw the ends of the tubes 15 and 17 within conduit 3. A more complete description of the apparatus will be set forth later.

A throttle valve 19 is disposed on conduit 3 upstream of the flow monitor and on the outlet side of the flow reactor (not shown) whereby the carrier gas from the flow reactor can be throttled, as is necessary for the isotopic enrichment of the mercury. Disposition of the throttle valve upstream of the flow monitor is quite important to the system. A throttle valve is important to the enrichment of the mercury feed stock because it controls the reactor pressure and if it is disposed downstream of the monitor, the monitor will not detect changes in the mercury density, which changes with the mercury flow rate.

Figure 2:
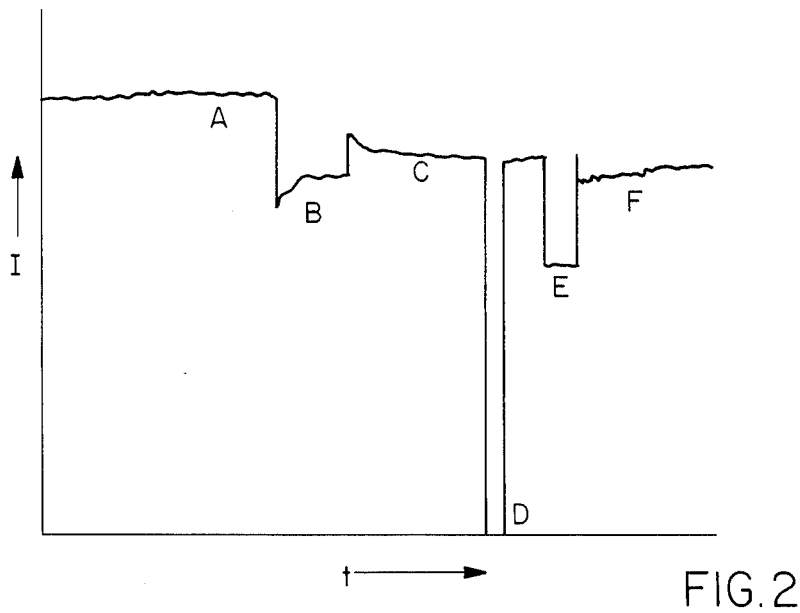
FIG. 2 is a trace of an analog recorder indicating absorption of 253.7 nm radiation on the ordinate and time on the abscissa.

In the continuous, in-line measurement of the quantity of mercury in a system, I have found the quantity of mercury vapor entrained between a pair of glass windows is proportional to the fractional absorption of an incident beam of 253.7 nm ultraviolet light passing through the system. In FIG. 2, a tracing is shown of the change in the transmitted signal of the flow monitor as a function of the flow reactor parameters. FIG. 2 plots intensity vs. time. In Region A of the trace, the plot of a nearly clean system is shown. No mercury was present in the detector when this region of the trace was recorded and the maximum signal is transmitted. When the mercury reservoir is opened, the mercury enters the system thereby changing the trace. Region B, with its attendant sharp drop in transmission, indicates that mercury has entered. Whe the carrier gas and inert gas (argon in this case) enters the system (but bypassing the mercruy reservoir) the trace changes, a shown in Region C. On the other hand, when the argon is passed through the mercury reservoir and the mercury is entrained in it, the trace shown in Region E is produced. When the monochrometer entrance slit is blocked, as shown in the the trace as Region D, no transmitted signal is indicated, and can be considered a zero level of transmission. Region F corresponds to identical conditions as those in Region E, that is the argon passing through the reaction vessel and entraining the mercury. In region F, however, there is a higher total pressure in the reactor vessel. In each of the Regions of the trace, the distance of the ultraviolet transmitting windows was identical and thus I conclude that the observed changes in the trace are representative of the changes in the absorbing mercury vapor density at the in-line flow monitor.

Figure 3:
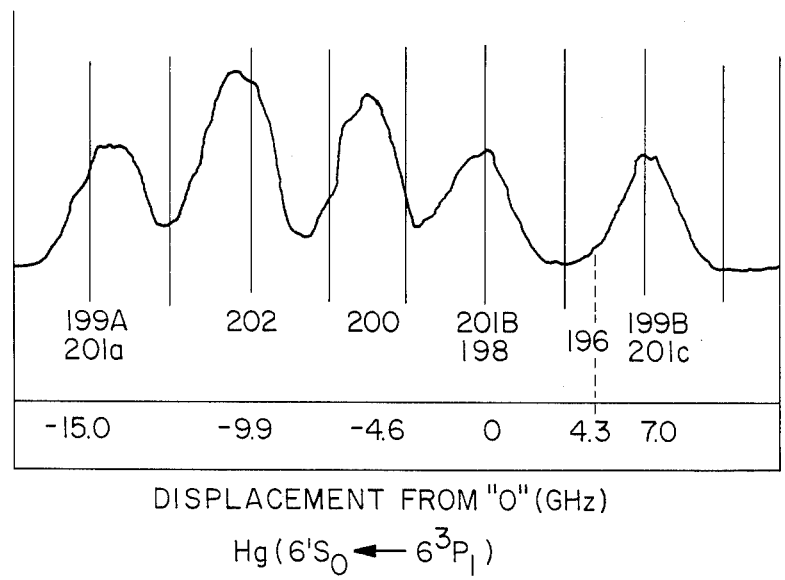
FIG. 3 is a trace showing typical emission of "natural" mercury with the emission lines of the isotopic forms of mercury and the mercury 196.

While the described trace of FIG. 2 can be an indication of the isotopic concentration of mercury by means of extrapolation, it is also possible to use a discharge of mercury isotopes as a mechanism for the generation of the trace. Such discharges are indicative of the particular isotope of mercury in the discharge device. In FIG. 3, a discharge of "natural" mercury is shown with its natural isotopic distribution. At the "zero" point on the trace, the central emission of the mercury 199A, 201a and 204 peak is at the −15.0 GHZ point. Mercury 199B and 201c emits a peak at the +7.0 GHZ point and mercury 196 center emits at +4.3 GHZ. The emission of any of these isotopes can be measured and the detection device can be configured to measure the attenuation of the amplitude of the emission due to absorption of the respective emission peak because of the isotope that is then resident in the the sensor provided proper "matching" of absorption peak and emission peak is carried out.

When measuring isotopes and using isotopic discharges, it is possible to use a high resolution Fabry-Perot interferometer as detector which can measure the differences in emission peaks and the transmitted emission peaks after absorption has taken place.

For example, if the emission source contained only one isotope, e.g. $Hg^{202}$, then the attenuation of this radiation would be primarily due to the absorption of $Hg^{202}$ in the effluent stream provided that the emission line did not overlap the other isotopes. In this case, measuring the signal level alone, e.g. with a low resolution monochrometer, is adequate for monitoring this isotope.

On the other hand, if the excitation lamp contained two isotopes, say $Hg^{204}$ and $Hg^{200}$, attentuation of the emission radiation could be due to the presence of $Hg^{204}$ and/or $Hg^{200}$ atoms. If the detector is a Fabry-Perot interferometer capable of monitoring 253.7 nm radiation, then the individual peaks can be monitored and, in principle, both the $Hg^{204}$ and $Hg^{200}$ absorption can be monitored.

Figure 4:
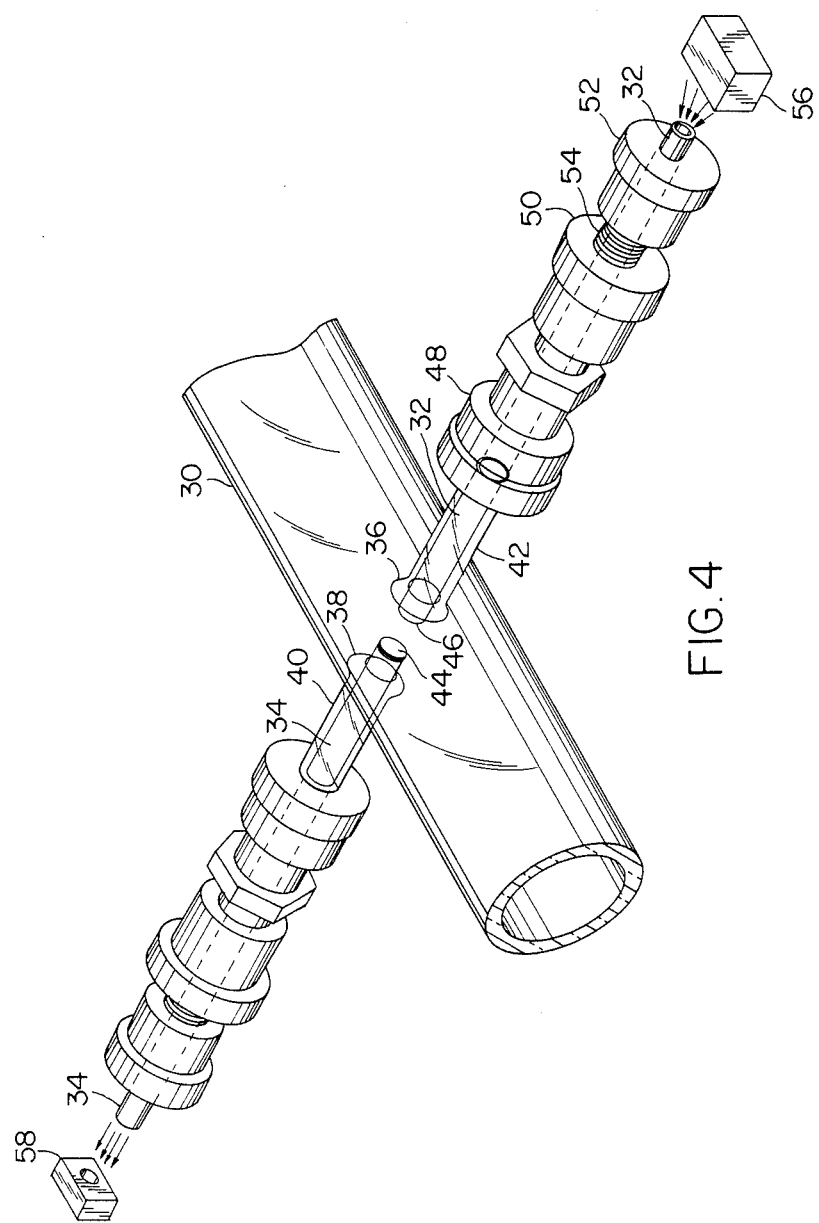
FIG. 4 is a perspective view, partially in cross section, showing the preferred embodiment of the sensor according to my invention.

Referring now to FIG. 4, the monitor is shown mounted across the diameter of a conduit 30. A pair of steel viewing tubes 32 and 34 are slidably arranged inside opposing apertures 36 and 38. A second pair of tubes 40 and 42, preferably made of glass, are sealed to conduit 30 at the apertures 36 and 38. A pair of thin windows 44 and 46 are sealed to the inner ends of the steel viewing tubes 32 and 34 and are arranged in a face to face relationship on the diameter of the conduit 30. Preferably the windows are made of quartz, generally less than about 0.1 cm. thick and are transparent to ultraviolet light at 253.7 nm. tubes 32 and 34 are slidably arranged within tubes 40 and 42 whereby the spacing between the windows 44 and 46 can be adjusted as required by the in-line flow monitoring process to give maximum sensitivity. The spacing between the windows is preferably from 0 to about 1.5 cm.

The monitor is hermetically sealed from the atmosphere by a sealing arrangement including, on one side, a pair of sealing nuts 48 and 50 that can be tightened or loosened upon O-rings (not shown), which, in turn, seal the system from the external atmosphere. The inner sealing nut 48 forces one of the O-rings against the glass tube 42 and the outer sealing nut forces the other O-ring upon the viewing tube 32. When sealing nut 50 is loosened, adjustment nut 52 can be turned upon threads 54 whereby viewing tube 32 can be moved along the diameter of conduit 30 thereby allowing changes in the spacing between windows 44 and 46. An identical sealing arrangement is used to hermetically seal viewing tube 34 and allow for its adjustment, as needed.

Light from a low pressure mercury source 56 enters the steel viewing tube 32 and emerges from quartz window 46. The light then passes across the gap between the window 46 and the window 44, whereby it then enters steel viewing tube 34 to be monitored by a detector 58 as described previously. Tuber 34 and detector 58 are located so that only a small solid angle (less than 10% of 4 pi steriadians) of the absorbing volume of Hg atoms between the windows is subtended. Thus, reradiated 253.7 nm radiation can be neglected. The attenuation of the amplitude of the observed emission versus the amplitude of the known emission from the known "natural" mercury source (or mercury isotope source) 56 is indicative of the quantity of mercury passing through the sensor and a continuous monitoring of these differences provides a continuous and in-line indication of the mercury or mercury isotope concentrations.

The following examples are provided to illustrate the present invention and its method of operation but are not to be construed as limitative upon the claims.

EXAMPLE 1

In the operation of the sensor, the separation between the windows was set at 1.0 cm. The carrier gas flow was 87 Standard Cubic Centimeters per minute SCC/minute). The attenuation of the signal relative to no mercury flow was 0.12. (This corresponds to a carrier gas pressure of 15 Torr). The calibration curve shows that for this attentuation, the mercury flow rate was 1.0 mg/hr. The calibration curve was formed by measuring, in a batch method, the amount of mercury accumulated in a downstream cold trap for a fixed time period for a particular attenuation. By changing the total pressure via throttle valve adjustment various attenuation values were obtained verses flow rates. For each total pressure, a new batch of Hg is collected and measured and corresponded to the observed flow rate described above.

EXAMPLE 2

The separation between the windows was 1.0 cm. The carrier gas flow was 87 SCC/minute. The attentuation of the signal relative to no mercury flow was 0.21 corresponding to a total carrier gas pressure of 0.9 Torr. The calibration curve shows that for this attenuation the mercury flow rate was 2.8 mg/hr. The calibration curve was obtained in the same manner as described in Example 1.

Accordingly, while there has been shown and described what are at present considered the preferred embodiments of the invention, it will be obvious to those skilled in the art that various changes and modifications may be made therein without departing from the scope of the invention as defined by the appended claims.

What is claimed is:

1. A sensor for measuring the rate at which mercury passes through a system adapted for use with a narrow wavelength ultraviolet light beam source and an ultraviolet light detector, said sensor comprising:
    means for forming a conduit for conveying mercury;
    a pair of apertures disposed face to face and arranged on opposite sides of said conduit;
    a pair of hollow support means, a portion of each being disposed inside of said conduit means and within one of said apertures;
    a pair of optically transparent windows one of said windows being disposed upon each of the internal ends of said hollow support means;
    means for adjusting the relative distance between the faces of said optically transparent windows;
    means for forming a vacuum seal;
    means for passing a narrow wavelength ultraviolet light beam through one of said windows, through the space between said windows and then through the other of said windows; and
    means for passing the ultraviolet light passing through the other of said windows to an ultraviolet light detector such that absorption of the ultraviolet light is continuously measured thereby giving an indication of the rate at which mercury passes between said windows.

2. A sensor in accordance with claim 1 wherein the window is optically transparent to radiation at 253.7 nm.

3. A sensor in accordance with claim 2 wherein the window is formed of a quartz glass.

4. A sensor in accordance with claim 2 further comprising a means for generating light at 253.7 nm and means for detecting the generated light, each of said means being separated from the other by said optically transparent windows.

5. A sensor in accordance with claim 2 further comprising means for changing the distance between each of said windows.

6. A sensor in accordance with claim 5 wherein each of the quartz windows are disposed upon a tubular member slidably arranged so as to enable variations in the spacing of the windows.

7. A sensor in accordance with claim 6 wherein the windows are disposed internally of said conduit.

8. A sensor in accordance with claim 4 wherein said generating means includes means to receive a multiplicity of ultraviolet emission sources, said sources containing isotopes of mercury and said detector being adapted to recognize the attenuation in the amplitude of the emission, such that the rate of mercury or mercury isotope passing through said sensor is measured.

9. A sensor in accordance with claim 1 further including a throttle valve disposed upstream of said sensor.

10. A sensor system for measuring the rate at which mercury passes through a system, said sensor system comprising:
    means for forming a conduit for conveying mercury;
    a pair of apertures disposed face to face and arranged on opposite sides of said conduit;
    a pair of hollow support means, a portion of each being disposed inside of said conduit means and within one of said apertures; and
    a pair of optically transparent windows one of said windows being disposed upon each of the internal ends of said hollow support means;
    means for forming a vacuum seal; and
    means for generating a narrow band width of ultraviolet light; and
    means for passing said narrow wavelength ultraviolet light beam through one of said windows, through the space between said windows and then through the other of said windows; and
    means for detecting the ultraviolet light passing through the other window such that absorption of the ultraviolet light is continuously measured thereby giving an indication of the rate at which mercury passes between said windows.

11. A sensor system in accordance with claim 10 wherein the window is optically transparent to radiation at 253.7 nm.

12. A sensor system in accordance with claim 11 wherein the window is formed of a quartz glass.

13. A sensor system in accordance with claim 11 wherein the ultraviolet light generating means generates light at 253.7 nm.

14. A sensor system in accordance with claim 11 further including means to change the distance between each of said windows.

15. A sensor system in accordance with claim 14 wherein each of the quartz windows are disposed upon a tubular member slidably arranged so as to enable variations in the spacing of the windows.

16. A sensor system in accordance with claim 15 wherein the windows are disposed internally of said conduit.

17. A sensor system in accordance with claim 10 wherein said generating means includes means to receive a multiplicity of ultraviolet emission sources, said sources containing isotopes of mercury and said detector being adapted to recognize the attenuation in the amplitude of the emission, such that the rate of mercury or mercury isotope flow in said sensor is measured.

18. A sensor system in accordance with claim 10 further including a throttle valve disposed upstream of said sensor.

19. A method of continuously monitoring the rate at which mercury flows through a system, said method comprising:
    passing mercury entrained in a carrier gas between a pair of windows, optically transparent to ultraviolet light; and
    transmitting ultraviolet light through one of said windows and receiving the ultraviolet light through the other of said windows; said light passing through said entrained mercury such that some of said light is absorbed by the mercury passing there between; and
    measuring the quantity of ultraviolet light absorbed by the mercury passing between said windows so as to continuously indicate the rate at which mercury flows through the system.

20. A method in accordance with claim 19 wherein the windows are optically transparent to radiation of 253.7 nm.

21. The method according to claim 19 further including recording the light absorbed by the mercury passing between said windows so as to give continuous readout of the rate of mercury flowing through said system.

* * * * *